United States Patent
Oowa et al.

(10) Patent No.: US 10,376,411 B2
(45) Date of Patent: Aug. 13, 2019

(54) ADJUSTER FOR AIRWAY SECURING DEVICE AND AIRWAY SECURING DEVICE

(71) Applicants: Takashima Sangyo Co. Ltd., Chino-shi, Nagano-ken (JP); KURUME UNIVERSITY, Kurume-shi, Fukuoka (JP)

(72) Inventors: Junji Oowa, Chino (JP); Jingo Kusukawa, Kurume (JP); Ryuichiro Tanoue, Kurume (JP); Kinuko Ogata, Kurume (JP)

(73) Assignees: Takashima Sangyo Co. Ltd. (JP); Kurume University (JP)

( * ) Notice: Subject to any disclaimer, the term of this patent is extended or adjusted under 35 U.S.C. 154(b) by 584 days.

(21) Appl. No.: 15/149,376

(22) Filed: May 9, 2016

(65) Prior Publication Data

US 2017/0135849 A1 May 18, 2017

(30) Foreign Application Priority Data

Nov. 12, 2015 (JP) ................. 2015-222078

(51) Int. Cl.
*A61F 5/56* (2006.01)
(52) U.S. Cl.
CPC .................... *A61F 5/566* (2013.01)
(58) Field of Classification Search
CPC ...... A61F 5/566; A61F 5/56; A61F 2005/563; A61F 5/58; A61F 5/0102; A61F 2005/0137; A61F 2005/0139; A61F 2005/0153; A61F 5/026; A61F 5/028; A61F 2210/009; A61F 2250/0067; A61F 2/0022; A61F 2/28; A61F 2/30; A61F 2/36; A61F 2/94; A61F 5/0125; A61F 5/055; A61F 2002/9528; A61F 2250/0004; A61F 2250/0065; A61F 2/013; A61F 2/14; A61F 2/82; A61F 2/95; A61F 5/013; A61F 9/007; A61F 9/00727; A61C 7/08; A61C 19/063; A61B 5/4547; A61B 5/4552; A61B 5/4557; A61B 5/682; A61B 5/0534; A63B 71/085; A63B 2071/086; A63B 2017/088; Y10S 602/902; A61N 2/00; A61N 2/002; A61N 2/004;

(Continued)

(56) References Cited

U.S. PATENT DOCUMENTS

2010/0132720 A1* 6/2010 Razmovski ............ A61F 5/566
128/848
2011/0308532 A1* 12/2011 Nelissen .................. A61C 7/36
128/848

FOREIGN PATENT DOCUMENTS

JP         5319421 B2 * 10/2013

* cited by examiner

*Primary Examiner* — Tarla R Patel
(74) *Attorney, Agent, or Firm* — Harness, Dickey & Pierce, P.L.C.

(57) ABSTRACT

In an adjuster for an airway securing device, a base member fixed to one of an upper jaw side attachment body and a lower jaw side attachment body is provided with a base member side half tube part and a slide member fixed to the other of the upper jaw side attachment body and the lower jaw side attachment body is provided with a slide member side half tube part. The base member side half tube part and the slide member side half tube part form a tube part in which an adjusting bolt is disposed on its inner peripheral side. A base member side flange part is formed at a base end of the base member side half tube part and a slide member side flange part shape is formed at a base end of the slide member side half tube part.

12 Claims, 8 Drawing Sheets

(58) Field of Classification Search
CPC .......... A61N 2/006; A61N 2/008; A61N 1/40; G09B 19/003; G09B 23/28; Y10T 29/49826

See application file for complete search history.

ADJUSTER FOR AIRWAY SECURING DEVICE AND AIRWAY SECURING DEVICE

CROSS-REFERENCE TO RELATED APPLICATION

This application claims priority to Japanese Application No. 2015-222078 filed Nov. 12, 2015, the entire disclosure of which is hereby incorporated by reference.

BACKGROUND OF THE INVENTION

Field of the Invention

The present invention relates to an adjuster for an airway securing device which is used in the airway securing device for treating a sleep apnea syndrome. Further, the present invention relates to an airway securing device provided with the adjuster.

Background

Conventionally, an airway securing device used for treatment of a sleep apnea syndrome has been known (see, for example, Japanese Patent No. 5319421). The airway securing device is a device structured to secure an airway during sleep by pulling a lower jaw of a patient to a front side. The airway securing device includes an upper jaw side attachment body which is attached to an upper jaw side in an oral cavity, a lower jaw side attachment body which is attached to a lower jaw side in the oral cavity, and an adjuster structured to move the lower jaw side attachment body with respect to the upper jaw side attachment body to adjust a relative position of the lower jaw side attachment body to the upper jaw side attachment body. The adjuster is structured of a base member, a slide member which is capable of sliding with respect to the base member, and an adjusting screw connecting the base member with the slide member. The base member is fixed to the upper jaw side attachment body through a wire member and a tip end part of the wire member is embedded in the upper jaw side attachment body. The slide member is fixed to the lower jaw side attachment body through a wire member and a tip end part of the wire member is embedded to the lower jaw side attachment body.

SUMMARY OF THE INVENTION

In the conventional airway securing device, when a relative position between the upper jaw side attachment body and the lower jaw side attachment body is to be adjusted, a large force may be acted on a connecting portion of the base member with the upper jaw side attachment body and a connecting portion of the slide member with the lower jaw side attachment body. However, in the conventional airway securing device, the tip end part of the wire member connecting the base member with the upper jaw side attachment body is embedded and fixed to the upper jaw side attachment body. Further, the tip end part of the wire member connecting the slide member with the lower jaw side attachment body is embedded and fixed to the lower jaw side attachment body. Therefore, in the airway securing device, it may be difficult to secure the fixed strength of the wire members to the upper jaw side attachment body and the lower jaw side attachment body.

Accordingly, in the airway securing device, in a case that a relative position of the upper jaw side attachment body to the lower jaw side attachment body is to be adjusted, when a large force is acted on a connecting portion of the base member with the upper jaw side attachment body or on a connecting portion of the slide member with the lower jaw side attachment body, the wire member may be come off from the upper jaw side attachment body or the lower jaw side attachment body. In other words, in the airway securing device, it may be difficult to secure the fixed strength of the adjuster to the upper jaw side attachment body and the lower jaw side attachment body and, as a result, when a relative position of the upper jaw side attachment body to the lower jaw side attachment body is to be adjusted, the adjuster may be come off from the upper jaw side attachment body or the lower jaw side attachment body.

In view of the problem described above, an objective of the present invention is to provide an adjuster for an airway securing device which is used in the airway securing device having an upper jaw side attachment body and a lower jaw side attachment body, the adjuster for an airway securing device being capable of securing fixed strength to the upper jaw side attachment body and the lower jaw side attachment body. Further, an objective of the present invention is to provide an airway securing device comprising the adjuster for an airway securing device.

In order to attain the objective, the present invention provides an adjuster for an airway securing device which is used in the airway securing device having an upper jaw side attachment body configured to be worn on an upper jaw side in an oral cavity of a patient and a lower jaw side attachment body configured to be worn on a lower jaw side in the oral cavity of the patient, the adjuster including a base member configured to be fixed to one of the upper jaw side attachment body and the lower jaw side attachment body, a slide member configured to be fixed to the other of the upper jaw side attachment body and the lower jaw side attachment body and capable of sliding with respect to the base member, and an adjusting bolt configured to slide the slide member with respect to the base member. The base member is provided with a base member side half tube part which is formed in a substantially half tube shape, the slide member is provided with a slide member side half tube part which is formed in a substantially half tube shape, and the base member side half tube part and the slide member side half tube part form a tube part in a substantially tube shape in which the adjusting bolt is disposed on its inner peripheral side. A base end of the base member side half tube part configured to be fixed to the one of the upper jaw side attachment body and the lower jaw side attachment body is formed with a base member side flange part which is enlarged in a flange shape, and a base end of the slide member side half tube part configured to be fixed to the other of the upper jaw side attachment body and the lower jaw side attachment body is formed with a slide member side flange part which is enlarged in a flange shape.

In the adjuster for an airway securing device in accordance with the present invention, a base end of the base member side half tube part configured to be fixed to the one of the upper jaw side attachment body and the lower jaw side attachment body is formed with a base member side flange part which is enlarged in a flange shape. Therefore, according to the present invention, an area of a portion of the base member fixed to the upper jaw side attachment body or the lower jaw side attachment body can be enlarged by utilizing the base member side flange part. Further, in the present invention, a base end of the slide member side half tube part configured to be fixed to the other of the upper jaw side attachment body and the lower jaw side attachment body is formed with a slide member side flange part which is enlarged in a flange shape. Therefore, an area of a portion of the slide member fixed to the upper jaw side attachment body or the lower jaw side attachment body can be enlarged by utilizing the slide member side flange part. Accordingly, in the present invention, fixed strength of the base member to the upper jaw side attachment body or the lower jaw side attachment body can be secured and fixed strength of the slide member to the upper jaw side attachment body or the lower jaw side attachment body can be secured. In other words, according to the present invention, the fixed strength of the adjuster to the upper jaw side attachment body and the lower jaw side attachment body can be secured.

The adjuster for an airway securing device in accordance with the present invention can be used in an airway securing device provided with the upper jaw side attachment body and the lower jaw side attachment body. In the airway securing device, for example, the base member side flange part is fixed to the one of the upper jaw side attachment body and the lower jaw side attachment body by potting resin which covers the base member side flange part, and the slide member side flange part is fixed to the other of the upper jaw side attachment body and the lower jaw side attachment body by potting resin which covers the slide member side flange part. In the airway securing device, the fixed strength of the adjuster to the upper jaw side attachment body and the lower jaw side attachment body can be secured.

In the conventional airway securing device, the base member is fixed to an upper jaw side attachment body through a wire member and the slide member is fixed to a lower jaw side attachment body through a wire member. Therefore, when large force is acted on a connecting portion of the base member with the upper jaw side attachment body or a connecting portion of the slide member and the lower jaw side attachment body, stress may be concentrated on the wire member, which is the connecting portion of the base member with the upper jaw side attachment body, or on the wire member which is the connecting portion of the slide member with the lower jaw side attachment body and, as a result, the wire member may be damaged. On the other hand, in the airway securing device in accordance with the present invention, the adjuster is fixed to the upper jaw side attachment body and the lower jaw side attachment body by potting resin which covers the base member side flange part and the slide member side flange part. Therefore, stress is hard to be concentrated on a particular portion of the connecting portion of the upper jaw side attachment body or the lower jaw side attachment body with the base member, or on a particular portion of the connecting portion of the upper jaw side attachment body or the lower jaw side attachment body with the slide member. Accordingly, the connecting portion of the upper jaw side attachment body or the lower jaw side attachment body with the base member is hard to be damaged, and the connecting portion of the upper jaw side attachment body or the lower jaw side attachment body with the slide member is hard to be damaged.

In addition, in the conventional airway securing device, when the adjuster is to be fixed to an upper jaw side attachment body and a lower jaw side attachment body, wire members are required to be buried in the upper jaw side attachment body and the lower jaw side attachment body and thus fixing work of the adjuster to the upper jaw side attachment body and the lower jaw side attachment body is complicated. On the other hand, in the airway securing device in accordance with the present invention, the adjuster is fixed to the upper jaw side attachment body and the lower jaw side attachment body by potting resin which covers the base member side flange part and the slide member side flange part and thus fixing work of the adjuster to the upper jaw side attachment body and the lower jaw side attachment body is easily performed.

As described above, in the present invention, the fixed strength of the adjuster to the upper jaw side attachment body and the lower jaw side attachment body can be secured.

DETAILED DESCRIPTION OF THE PREFERRED EMBODIMENT

An embodiment of the present invention will be described below with reference to the accompanying drawings.
(Entire Structure of Airway Securing Device)

Figure 1:
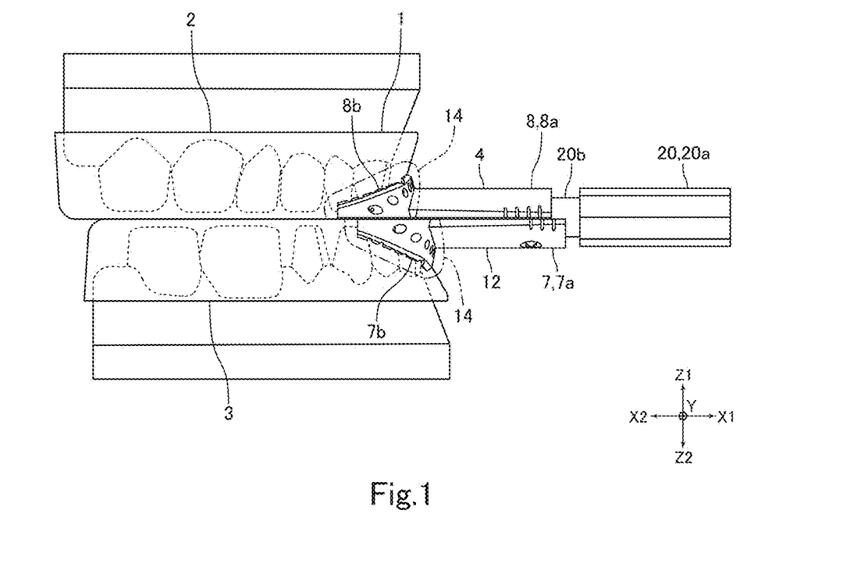
FIG. 1 is a view schematically showing a state that an airway securing device in accordance with an embodiment of the present invention is worn on a patient.

FIG. 1 is a view schematically showing a state that an airway securing device 1 in accordance with an embodiment of the present invention is worn on a patient.

An airway securing device 1 in this embodiment is a device structured to secure an airway during sleep by adjusting a position of a lower jaw of a patient and is used to treat a sleep apnea syndrome. The airway securing device 1 includes an upper jaw side attachment body (mouthpiece) 2 which is worn on an upper jaw side in an oral cavity of a patient, a lower jaw side attachment body (mouthpiece) 3 which is worn on a lower jaw side in the oral cavity of the patient, and an adjuster 4 for adjusting a relative position between the upper jaw side attachment body 2 and the lower jaw side attachment body 3. The upper jaw side attachment body 2 and the lower jaw side attachment body 3 are separately formed from each other and are connected with each other by the adjuster 4.

The upper jaw side attachment body 2 is formed in a shape along a tooth row on the upper jaw side and the lower jaw side attachment body 3 is formed in a shape along a tooth row on the lower jaw side. Specifically, the upper jaw side attachment body 2 is formed so that the upper jaw side attachment body 2 is fitted to the upper jaw side in the oral cavity in a state that there is substantially no space between teeth and gums on the upper jaw side and the upper jaw side attachment body 2. Further, the lower jaw side attachment body 3 is formed so that the lower jaw side attachment body 3 is fitted to the lower jaw side in the oral cavity in a state that there is substantially no space between teeth and gums on the lower jaw side and the lower jaw side attachment body 3. The upper jaw side attachment body 2 and the lower jaw side attachment body 3 are normally produced by pouring synthetic resin in a mold which is prepared for each patient.

In the following descriptions, a side where the upper jaw side attachment body 2 is disposed with respect to the lower jaw side attachment body 3 ("Z1" direction side in FIG. 1 and the like) is referred to as an "upper" side, and the opposite side ("Z2" direction side in FIG. 1 and the like) is referred to as a "lower" side. Further, a side which is disposed on a front face side with respect to a face of a patient when the airway securing device 1 is worn on the patient ("X1" direction side in FIG. 1 and the like) is referred to as a "front" side, and the opposite side ("X2" direction side in FIG. 1 and the like) is referred to as a "rear (back) side". In addition, a direction perpendicular to the upper and lower direction and the front and rear direction ("Y" direction in FIG. 1 and the like) is referred to as a "right and left direction".

(Structure of Adjuster)

Figure 2:
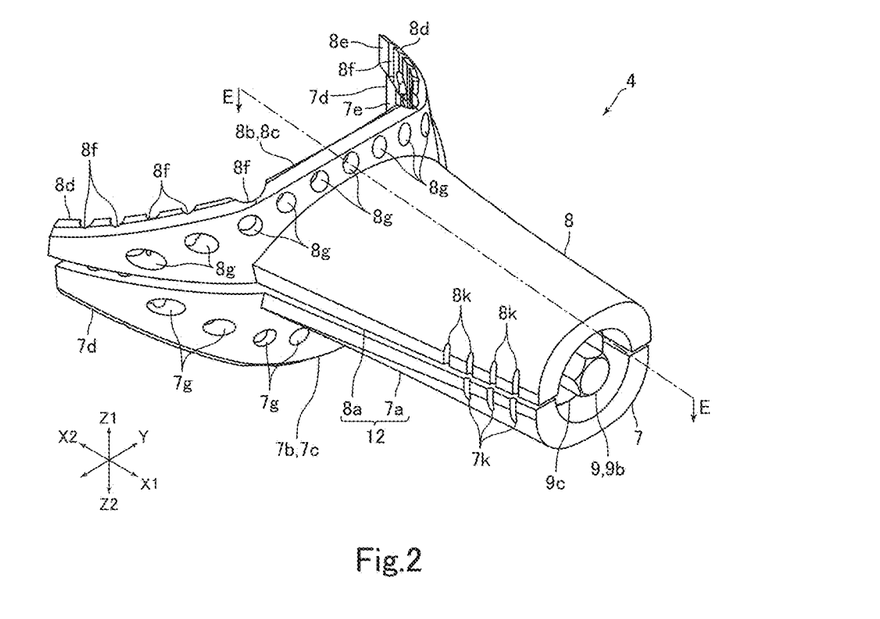
FIG. 2 is a perspective view showing an adjuster in FIG. 1.
Figure 3:
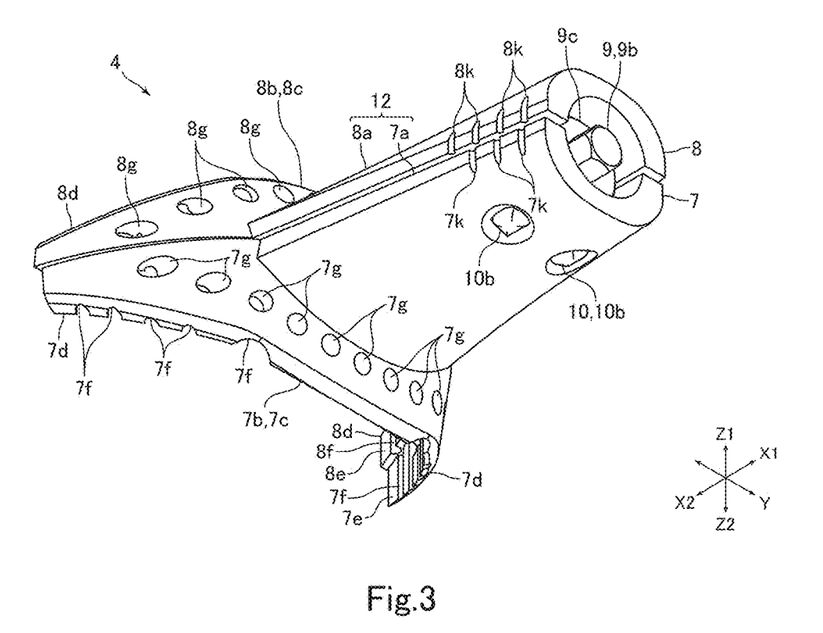
FIG. 3 is a perspective view showing the adjuster in FIG. 2 which is viewed in another direction.
Figure 4:
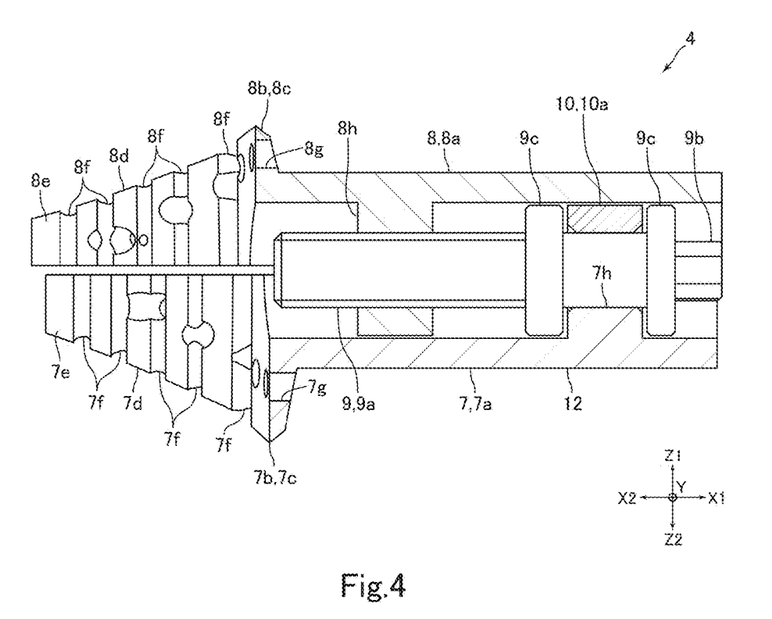
FIG. 4 is a cross-sectional view showing the "E-E" cross section in FIG. 2.
Figure 5:
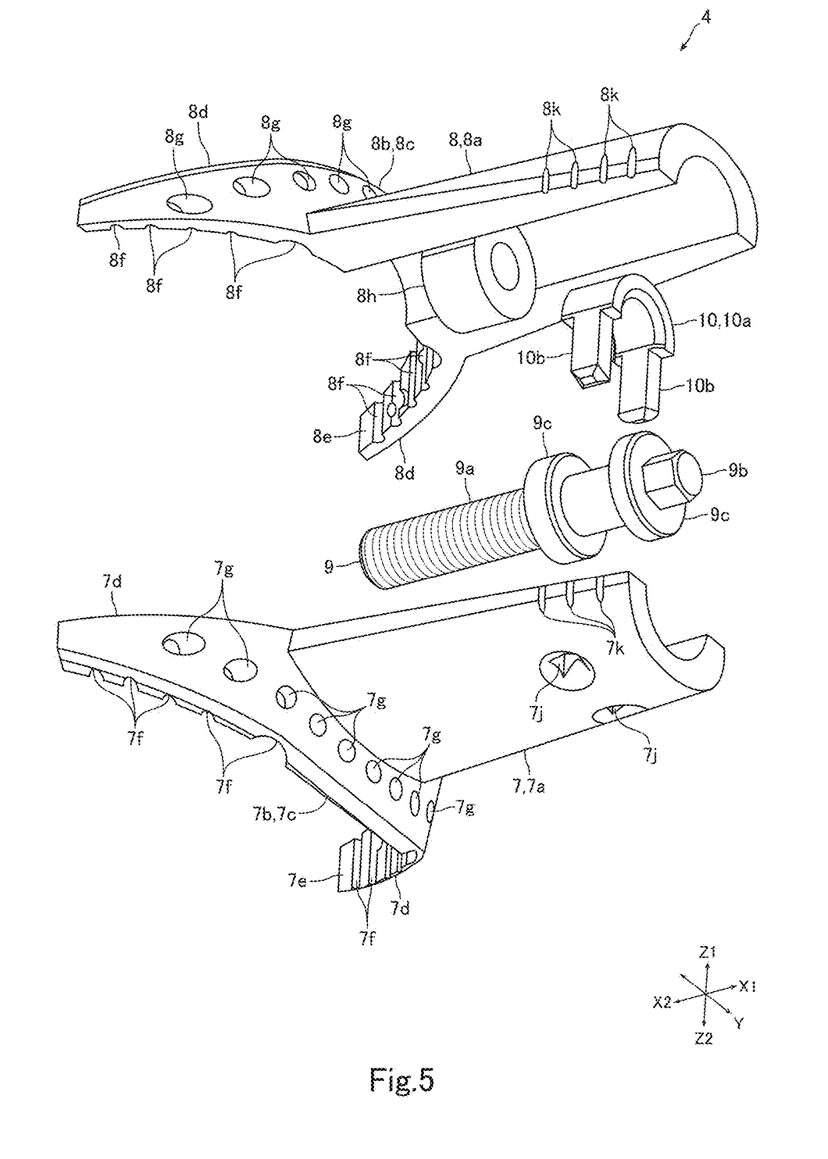
FIG. 5 is an exploded perspective view showing the adjuster in FIG. 3.
Figure 6:
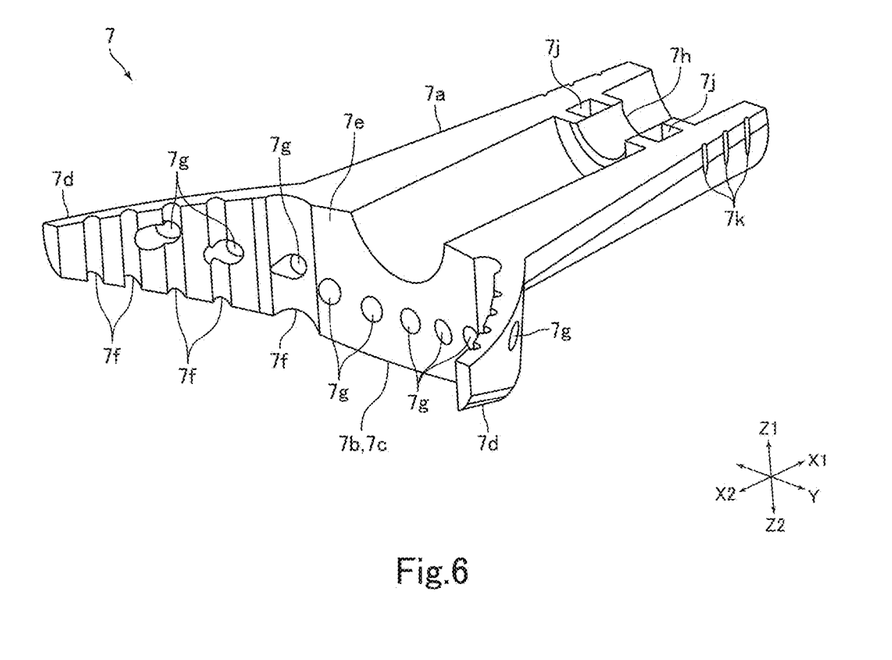
FIG. 6 is a perspective view showing a base member in FIG. 2.

FIG. 2 is a perspective view showing the adjuster 4 in FIG. 1. FIG. 3 is a perspective view showing the adjuster 4 in FIG. 2 which is viewed in another direction. FIG. 4 is a cross-sectional view showing the "E-E" cross section in FIG. 2. FIG. 5 is an exploded perspective view showing the adjuster 4 in FIG. 3. FIG. 6 is a perspective view showing a base member 7 in FIG. 2.

The adjuster 4 structures a part of the airway securing device 1 as described above and is used in the airway securing device 1. The adjuster 4 is fixed to the front end sides of the upper jaw side attachment body 2 and the lower jaw side attachment body 3. In other words, a rear end side of the adjuster 4 is fixed to the upper jaw side attachment body 2 and the lower jaw side attachment body 3. The adjuster 4 is structured of a base member 7 which is fixed to the lower jaw side attachment body 3, a slide member 8 which is fixed to the upper jaw side attachment body 2 and is slidable with respect to the base member 7, an adjusting bolt 9 for making the slide member 8 slide in the front and rear direction with respect to the base member 7, and an attaching member 10 for attaching the adjusting bolt 9 to the base member 7.

The base member 7, the slide member 8, the adjusting bolt 9 and the attaching member 10 are formed of synthetic resin. In other words, all parts of the adjuster 4 including the adjusting bolt 9 are formed of synthetic resin. Specifically, the base member 7, the slide member 8, the adjusting bolt 9 and the attaching member 10 are formed of engineering plastic such as polyetheretherketone or polyacetal whose strength is relatively high and has no biological toxicity (or, its biological toxicity is low).

The base member 7 is provided with a half tube part 7a as a base member side half tube part which is formed in a substantially half tube shape. The slide member 8 is provided with a half tube part 8a as a slide member side half tube part which is formed in a substantially half tube shape. In the adjuster 4, a tube part 12 in a substantially tube shape in which an adjusting bolt 9 is disposed on its inner peripheral side is formed of the half tube part 7a and the half tube part 8a. The half tube part 7a structures a lower side half of the tube part 12 and the half tube part 8a structures an upper side half of the tube part 12. A rear end (base end) of the tube part 12 is fixed to the upper jaw side attachment body 2 and the lower jaw side attachment body 3.

The half tube parts 7a and 8a in this embodiment are formed in a substantially half elliptical tube shape, and the tube part 12 is formed in a substantially elliptical tube shape. A cross sectional shape of the tube part 12 perpendicular to the front and rear direction is formed in a substantially elliptical shape whose major axis direction is the right and left direction and its minor axis direction is the upper and lower direction. An outward form of the tube part 12 becomes smaller from a rear end (base end) of the tube part 12 toward a front end (tip end) of the tube part 12. In other words, the base end side of the tube part 12 is larger in width and the tip end side of the tube part 12 is smaller in width. Specifically, the outward form of the tube part 12 is formed in a substantially truncated elliptical cone shape whose outer diameter gradually becomes smaller (continuously becomes smaller) as going toward the front end of the tube part 12. An inner peripheral face of the tube part 12 is formed in a cylindrical face shape whose inner diameter is substantially constant.

The adjusting bolt 9 is disposed on an inner peripheral side of the tube part 12 so that an axial direction of the adjusting bolt 9 is coincided with the front and rear direction. Further, the adjusting bolt 9 is rotatably held by the base member 7. A rear end portion of the adjusting bolt 9 is provided with a screw part 9a whose outer peripheral face is formed with a male screw. A front end side portion of the adjusting bolt 9 is formed as an engaging part 9b structured to engage with a screwdriver 20 described below (see FIG. 1). The engaging part 9b is formed in a polygonal-column shape such as a hexagonal column shape. Two flange parts 9c in a circular ring shape which are enlarged to an outer side in a radial direction of the adjusting bolt 9 are formed on a rear side of the engaging part 9b. The two flange parts 9c are separately formed from each other with a predetermined space therebetween in the front and rear direction. The screw part 9a is formed on a rear side of the rear side flange part 9c of the two flange parts 9c.

A flange part 7b as a base member side flange part which is enlarged in a flange shape is formed at a rear end (base end) of the half tube part 7a which is fixed to the lower jaw side attachment body 3. The flange part 7b is integrally formed with the half tube part 7a. Further, the flange part 7b is structured of a first flange part 7c and a second flange part 7d as a curved plate part. The first flange part 7c is enlarged toward a lower side from the rear end of the half tube part 7a. The second flange part 7d is formed in a curved plate shape and is enlarged from the rear end of the half tube part 7a and the first flange part 7c so as to be along a tooth row on the lower jaw side of a patient. In other words, the second flange part 7d is enlarged from the rear end of the half tube part 7a and the first flange part 7c toward both sides in the right and left direction and toward the rear side.

A flange part 8b as a slide member side flange part which is enlarged in a flange shape is formed at a rear end (base end) of the half tube part 8a which is fixed to the upper jaw side attachment body 2. The flange part 8b is integrally formed with the half tube part 8a. Further, the flange part 8b is structured of a first flange part 8c and a second flange part 8d as a curved plate part. The first flange part 8c is enlarged toward an upper side from the rear end of the half tube part 8a. The second flange part 8d is formed in a curved plate shape and is enlarged from the rear end of the half tube part 8a and the first flange part 8c so as to be along a tooth row on the upper jaw side of the patient. In other words, the second flange part 8d is enlarged from the rear end of the half tube part 8a and the first flange part 8c toward both sides in the right and left direction and toward the rear side.

A rear face of the flange part 7b is formed as an abutting face 7e structured to abut with a front face of the lower jaw side attachment body 3. The abutting face 7e is formed in a curved face shape having substantially the same curvature as a curvature of the tooth row on the lower jaw side. The abutting face 7e is formed with a plurality of grooves 7f. The groove 7f is formed in a vertical groove shape which is recessed toward the front side and is continuously formed from an upper end of the flange part 7b to its lower end. A cross sectional shape of the groove 7f perpendicular to the upper and lower direction is a circular arc shape. Further, a plurality of the grooves 7f is formed with a predetermined pitch in a direction that the second flange part 7d is enlarged (direction along a tooth row on the lower jaw side of the patient). As described above, the abutting face 7e is formed with a plurality of the grooves 7f with a predetermined pitch and thus the abutting face 7e is formed in a concave-convex face (protruded and recessed face). In this embodiment, as shown in FIG. 6, the groove 7f is not formed on a center portion of the abutting face 7e.

A rear face of the flange part 8b is formed as an abutting face 8e structured to abut with a front face of the upper jaw side attachment body 2. The abutting face 8e is formed in a curved face shape having substantially the same curvature as a curvature of the tooth row on the upper jaw side. The abutting face 8e is also formed with a plurality of grooves 8f which are formed similarly to the grooves 7f. The groove 8f is formed in a vertical groove shape which is recessed toward the front side and is continuously formed from an upper end of the flange part 8b to its lower end. Further, a plurality of the grooves 8f is formed with a predetermined pitch in a direction that the second flange part 8d is enlarged (direction along a tooth row on the upper jaw side of a patient). In this embodiment, a plurality of the grooves 8f is disposed with the same pitch as that of a plurality of the grooves 7f. As described above, the abutting face 8e is formed with a plurality of the grooves 8f with a predetermined pitch and thus the abutting face 8e is formed in a concave-convex face (protruded and recessed face). In this embodiment, similarly to the abutting face 7e, the groove 8f is not formed on a center portion of the abutting face 8e.

The flange part 7b is formed with a plurality of through-holes 7g penetrating through the flange part 7b. The through-hole 7g is formed so as to penetrate through the flange part 7b in the front and rear direction. Further, a plurality of the through-holes 7g is formed with a predetermined pitch in the right and left direction. The flange part 8b is, similarly to the flange part 7b, formed with a plurality of through-holes 8g penetrating through the flange part 8b. The through-hole 8g is formed so as to penetrate through the flange part 8b in the front and rear direction. Further, a plurality of the through-holes 8g is formed with a predetermined pitch in the right and left direction. In this embodiment, a plurality of the through-holes 8g is disposed with the same pitch as that of a plurality of the through-holes 7g.

A screw engaging part 8h in a cylindrical tube shape is, as shown in FIG. 5, formed on an inner peripheral side of the half tube part 8a formed in a substantially half elliptical tube shape (in other words, at a center on an under face side of the half tube part 8a). The screw engaging part 8h is formed on a rear end side of the half tube part 8a. An inner peripheral face of the screw engaging part 8h is formed with a female screw with which the screw part 9a of the adjusting bolt 9 is engaged. As shown in FIG. 4, the screw part 9a is inserted into an inner peripheral side of the screw engaging part 8h and the screw part 9a is engaged with the female screw formed on the inner peripheral face of the screw engaging part 8h.

A bolt holding part 7h in a half cylindrical tube shape is, as shown in FIG. 6, formed on an inner peripheral side of the half tube part 7a formed in a substantially half elliptical tube shape (in other words, at a center on an upper face side of the half tube part 7a). The bolt holding part 7h is formed on a front end side of the half tube part 7a. Through-holes 7j penetrating in the upper and lower direction are formed on both end sides in the right and left of the bolt holding part 7h. The attaching member 10 is, as shown in FIG. 5, structured of a bolt holding part 10a formed in a half cylindrical tube shape and two shaft parts 10b inserted into through-holes 7j. The attaching member 10 is fixed to the half tube part 7a so that a portion of the adjusting bolt 9 between the two flange parts 9c is sandwiched between the bolt holding part 7h and the bolt holding part 10a. Further, the attaching member 10 is fixed to the half tube part 7a by caulking in a state that the shaft parts 10b are inserted into the through-holes 7j from an upper side.

The adjusting bolt 9 is rotatably held by the half tube part 7a through the bolt holding part 7h and the bolt holding part 10a. An inner diameter of a cylindrical tube shaped portion structured of the bolt holding part 7h and the bolt holding part 10a is set to be smaller than outer diameters of the flange parts 9c and thus movement in the front and rear direction of the adjusting bolt 9 is restricted by the two flange parts 9c and the bolt holding parts 7h and 10a. A front end of the adjusting bolt 9 is disposed on a rear side relative to a front end of the half tube part 7a. In other words, a tip end of the adjusting bolt 9 disposed on the tip end side of the half tube part 7a is disposed to a base end side of the half tube part 7a relative to the tip end of the half tube part 7a.

The base member 7 and the slide member 8 are integrated with each other in a state that the screw part 9a of the adjusting bolt 9 is engaged with an inner peripheral face of the screw engaging part 8h of the slide member 8. Further, when the adjusting bolt 9 is turned in a state that the base member 7 and the slide member 8 are integrated with each other, the slide member 8 is moved in the front and rear direction with respect to the base member 7. In this embodiment, one ends or both ends in the right and left direction of the half tube parts 7a and 8a are formed with a plurality of cutting grooves 7k and 8k which are marks for visually confirming a displacement amount in the front and rear direction between the base member 7 and the slide member 8. The cutting grooves 7k and 8k are formed in a vertical groove shape.

The base end of the half tube part 7a and the flange part 7b are fixed to the lower jaw side attachment body 3. Specifically, the base end of the half tube part 7a and the flange part 7b are, as shown in FIG. 1, fixed to the lower jaw side attachment body 3 by potting resin 14 which covers the flange part 7b. The base end of the half tube part 8a and the flange part 8b are fixed to the upper jaw side attachment body 2. Specifically, the base end of the half tube part 8a and the flange part 8b are fixed to the upper jaw side attachment body 2 by potting resin 14 which covers the flange part 8b. In other words, the base end of the half tube part 7a and the flange part 7b are fixed to the lower jaw side attachment body 3 and the base end of the half tube part 8a and the flange part 8b are fixed to the upper jaw side attachment body 2 by potting using resin such as urethane resin or acryl resin which has been widely used for a dental technique.

(Using Method of Airway Securing Device)

When the airway securing device 1 is to be used, for example, the upper jaw side attachment body 2 and the lower jaw side attachment body 3 are put in the oral cavity of a patient who lies on his (her) back so that the upper jaw side attachment body 2 is fitted and worn on the teeth and the gums on the upper jaw side and the lower jaw side attachment body 3 is fitted and worn on the teeth and the gums on lower jaw side. In this state, the adjusting bolt 9 is turned so that the upper jaw side attachment body 2 is entered into the oral cavity and the lower jaw side attachment body 3 is drawn to a front side with respect to the face of the patient. A drawing amount of the lower jaw side attachment body 3 is adjusted by a turning amount of the adjusting bolt 9 corresponding to the patient using it. When the lower jaw side attachment body 3 is drawn to the front side with respect to the face, the lower jaw side of the patient is drawn to the front side and thus a tongue root of the patient is also drawn to the front side and the airway is secured.

When the adjusting bolt 9 is to be turned, as shown in FIG. 1, an adjusting screwdriver 20 is used. The screwdriver 20 is structured of a main body part 20a formed in a polygonal column shape such as an octagonal column shape and an engaging part 20b in a cylindrical tube shape which is connected with one end side of the main body part 20a. An engaging hole configured to engage with the engaging part 9b of the adjusting bolt 9 is formed on an inner peripheral side of the engaging part 20b. In a state that the engaging part 9b is engaged with an inner peripheral side of the engaging part 20b, the adjusting bolt 9 is turned by turning the screwdriver 20.

(Principal Effects in this Embodiment)

As described above, in this embodiment, the flange part 7b is formed at a base end of the half tube part 7a of the base member 7, and the base end of the half tube part 7a and the flange part 7b is fixed to the lower jaw side attachment body 3 by the potting resin 14 which covers the flange part 7b. Therefore, according to this embodiment, an area of a portion of the base member 7 fixed to the lower jaw side attachment body 3 can be enlarged by utilizing the flange part 7b. Further, in this embodiment, the flange part 8b is formed at a base end of the half tube part 8a of the slide member 8, and the base end of the half tube part 8a and the flange part 8b is fixed to the upper jaw side attachment body 2 by the potting resin 14 which covers the flange part 8b. Therefore, according to this embodiment, an area of a portion of the slide member 8 fixed to the upper jaw side attachment body 2 can be enlarged by utilizing the flange part 8b. Accordingly, in this embodiment, the fixed strength of the base member 7 to the lower jaw side attachment body 3 can be secured and the fixed strength of the slide member 8 to the upper jaw side attachment body 2 can be secured. In other words, according to this embodiment, the fixed strength of the adjuster 4 to the upper jaw side attachment body 2 and the lower jaw side attachment body 3 can be secured.

Especially, in this embodiment, the flange part 7b is provided with the second flange part 7d which is enlarged along a tooth row on a lower jaw side of a patient and thus an area of a portion of the base member 7 fixed to the lower jaw side attachment body 3 can be further enlarged. Further, in this embodiment, the flange part 8b is provided with the second flange part 8d which is enlarged along a tooth row on an upper jaw side of the patient and thus an area of a portion of the slide member 8 fixed to the upper jaw side attachment body 2 can be further enlarged. Therefore, according to this embodiment, the fixed strength of the adjuster 4 to the upper jaw side attachment body 2 and the lower jaw side attachment body 3 can be increased.

In this embodiment, a plurality of the grooves 7f is formed on the abutting face 7e of the flange part 7b which is abutted with a front face of the lower jaw side attachment body 3 and a plurality of the grooves 8f is formed on the abutting face 8e of the flange part 8b which is abutted with a front face of the upper jaw side attachment body 2. Further, a plurality of the through-holes 7g is formed in the flange part 7b and a plurality of the through-holes 8g is formed in the flange part 8b. Therefore, according to this embodiment, the fixed strength of the flange part 7b to the lower jaw side attachment body 3 and the fixed strength of the flange part 8b to the upper jaw side attachment body 2 can be increased by the potting resin 14 which is entered into and hardened in the grooves 7f and 8f and the through-holes 7g and 8g. In other words, in this embodiment, the fixed strength of the adjuster 4 to the upper jaw side attachment body 2 and the lower jaw side attachment body 3 can be increased by an anchoring effect.

In this embodiment, the adjuster 4 is fixed to the upper jaw side attachment body 2 and the lower jaw side attachment body 3 by the potting resins 14 which cover the flange parts 7b and 8b. Therefore, according to this embodiment, in a case that a relative position between the upper jaw side attachment body 2 and the lower jaw side attachment body 3 is to be adjusted, even when large force is acted on a connecting portion of the base member 7 with the lower jaw side attachment body 3 and a connecting portion of the slide member 8 with the upper jaw side attachment body 2, stress is hard to be concentrated on a particular portion of the connecting portion of the base member 7 with the lower jaw side attachment body 3 and a particular portion of the connecting portion of the slide member 8 with the upper jaw side attachment body 2. Accordingly, in this embodiment, the connecting portion of the base member 7 with the lower jaw side attachment body 3 and the connecting portion of the slide member 8 with the upper jaw side attachment body 2 are hard to be damaged.

In this embodiment, the base member 7 and the slide member 8 are fixed to the upper jaw side attachment body 2 and the lower jaw side attachment body 3 by the potting resins 14 which cover the flange parts 7b and 8b. Therefore, according to this embodiment, fixing work of the base member 7 to the lower jaw side attachment body 3 and fixing work of the slide member 8 to the upper jaw side attachment body 2 are easily performed. Especially, in this embodiment, the grooves 7f and 8f and the through-holes 7g and 8g are formed in the flange parts 7b and 8b and thus the flange parts 7b and 8b are easily elastically deformed. Therefore, the abutting face 7e of the flange part 7b can be easily abutted with the lower jaw side attachment body 3 and the abutting face 8e of the flange part 8b can be easily abutted with the upper jaw side attachment body 2. Accordingly, in this embodiment, the fixing work of the base member 7 to the lower jaw side attachment body 3 and the fixing work of the slide member 8 to the upper jaw side attachment body 2 are further easily performed.

In this embodiment, an outward form of the tube part 12 becomes smaller as going to the front end of the tube part 12 from the rear end of the tube part 12. In other words, in this embodiment, an outward form on the front end side of the tube part 12 with which lips of a patient are to be touched becomes small. Therefore, according to this embodiment, discomfort of a patient can be restrained when the airway securing device 1 is worn. Accordingly, the patient is hard to feel discomfort when the airway securing device 1 is worn and, as a result, the patient is easy to use the airway securing device 1 continuously. Further, in this embodiment, an outward form on the rear end side of the tube part 12 is large and thus lowering of strength of the tube part 12 can be restrained.

In this embodiment, the front end of the adjusting bolt 9 is disposed on a rear side relative to the front end of the half tube part 7a of the base member 7 and thus a patient is hard to contact with the adjusting bolt 9. Therefore, according to this embodiment, a sleeping patient can be prevented from unconsciously touching the adjusting bolt 9 and, when the airway securing device 1 is to be washed, a patient or the like can be prevented from touching the adjusting bolt 9. Accordingly, in this embodiment, after having been adjusted once, displacement of a relative position between the upper jaw side attachment body 2 and the lower jaw side attachment body 3 can be prevented. Further, an injury of a patient or the like caused by touching the adjusting bolt 9 can be prevented.

In this embodiment, all parts of the adjuster 4 including the adjusting bolt 9 are formed of synthetic resin. Therefore, according to this embodiment, even a patient having a metal allergy, the airway securing device 1 can be used without anxiety. Further, all parts of the adjuster 4 can be, for example, produced by injection molding and thus cost of the adjuster 4 can be reduced.

(Clinical Effects of Airway Securing Device)

FIGS. 7(A), 7(B) 7(C) and 7(D) are graphs showing an example of clinical data of a patient who has used the airway securing device 1 shown in FIG. 1. FIG. 8 is an example of cephalometric radiographs of a patient wearing the airway securing device 1 shown in FIG. 1.

Figure 7A:
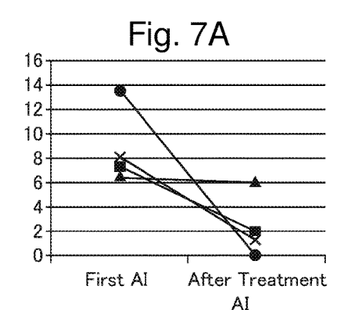
FIGS. 7(A), 7(B) 7(C) and 7(D) are graphs showing an example of clinical data of a patient who has used the airway securing device shown in FIG. 1.
Figure 7B:
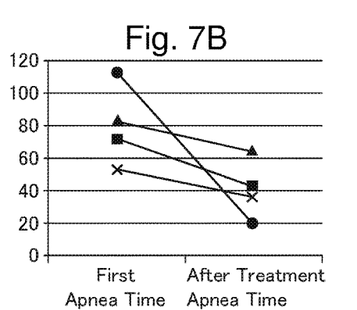
Figure 7C:
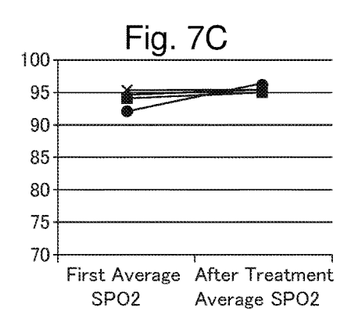
Figure 7D:
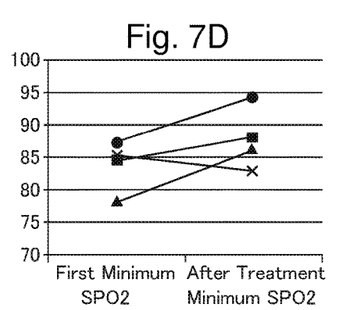
Figure 8:
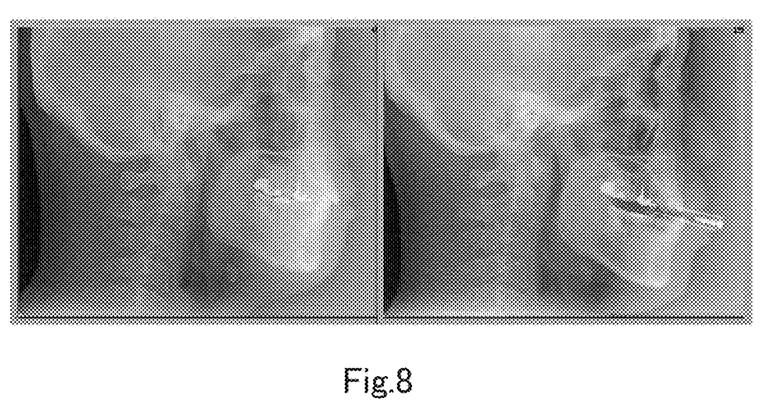
FIG. 8 is an example of cephalometric radiographs of a patient wearing the airway securing device shown in FIG. 1.

As a result of performing sleep polysomnography inspections (PSG inspection) by using the airway securing device 1 in this embodiment, lowering of "AI" was recognized in all cases (see FIG. 7(A)). The average of improved rates of "AI" is 65.99±34.39%, which indicates effectiveness of a treatment using the airway securing device 1. Further, an apnea time was also improved except one case (see FIG. 7(B)) and the apnea time was shortened for 26.35±37.56 seconds on average. In addition, the minimum "SPO2" was not improved in two cases but the average "SPO2" of all the cases was improved (see FIGS. 7(C) and 7(D)) and a satisfactory treatment effect was obtained.

The "PSG inspection" is an inspection in which sensors for measuring, for example, brain wave, respiratory movement, an electrocardiogram, a snoring sound, an oxygen saturation degree of a body are attached to a patient to perform recording continuously all night long. The "PSG inspection" is used for a conclusive diagnosis of the sleep apnea syndrome (SAS). Further, the "AI" is a numerical value which is obtained by dividing the total number of apneas during sleep by sleeping hours to calculate a value per hour. The higher the numerical value is, the severity of the SAS becomes higher. In addition, an "apnea time" is a time period of apneas during sleep. Further, the "SPO2" is arterial oxygen saturation which indicates a saturation degree of oxygen in blood by a percent. The lower the numerical value is, the severity of the SAS becomes higher.

When the cephalometric radiograph is analyzed, the forward moving amount of a lower jaw by the airway securing device 1 and increase of the airway diameter are seen to have correlation (see FIG. 8). In FIG. 8, the photograph on the left side is that of a state that the airway securing device 1 is not worn and the photograph on the right side is that of a state that the airway securing device 1 is worn. In 32 cases in which the airway securing device 1 was used, a total of two adverse events were found, i.e., one was dryness of the mouth and one was pain of a lower jaw front tooth. However, regarding the pain of the tooth, the symptom was improved by moving the lower jaw position to a rear side a little and the treatment using the airway securing device 1 was capable of being continued. In a conventional fixed type airway securing device, an adjusting time for the airway securing device was about 30 minutes. However, in the airway securing device 1 in this embodiment, an adjusting time for the airway securing device 1 was several minutes. Therefore, when the airway securing device 1 in this embodiment is used, a load of a patient can be also reduced in addition to an operator such as a doctor.

(Other Embodiments)

In the embodiment described above, the abutting face 7e is formed in a concave-convex face by forming a plurality of the grooves 7f on the abutting face 7e of the flange part 7b. However, for example, the abutting face 7e may be formed in a concave-convex face by forming a plurality of recessed parts in a circular shape or a polygonal shape on the abutting face 7e. Similarly, for example, the abutting face 8e may be formed in a concave-convex face by forming a plurality of recessed parts in a circular shape or a polygonal shape on the abutting face 8e. Further, in the embodiment described above, no grooves 7f and 8f may be formed on the abutting faces 7e and 8e. In other words, the abutting faces 7e and 8e may be formed in a curved face having no concave and convex. Further, in the embodiment described above, no through-holes 7g and 8g may be formed.

In the embodiment described above, the flange part 7b is enlarged toward a lower side from a rear end of the half tube part 7a and is enlarged so as to be along a tooth row on a lower jaw side of a patient. However, the flange part 7b is not required to be enlarged toward a lower side from a rear end of the half tube part 7a, or the flange part 7b is not required to be enlarged along a tooth row on the lower jaw side. Similarly, in the embodiment described above, the flange part 8b is enlarged toward an upper side from a rear end of the half tube part 8a and is enlarged so as to be along a tooth row on an upper jaw side of a patient. However, the flange part 8b is not required to be enlarged toward an upper side from a rear end of the half tube part 8a, or the flange part 8b is not required to be enlarged along a tooth row on the upper jaw side.

In the embodiment described above, an outward form of the tube part 12 becomes continuously smaller as going toward a front end of the tube part 12 from a rear end of the tube part 12. However, an outward form of the tube part 12 may become stepwisely smaller as going toward a front end of the tube part 12 from a rear end of the tube part 12. In other words, steps may be formed on an outer peripheral face of the tube part 12. Further, in the embodiment described above, an outward form of the tube part 12 becomes smaller as going toward a front end of the tube part 12 from a rear end of the tube part 12. However, an outward form of the tube part 12 may be formed so that its size from a rear end of the tube part 12 to a front end of the tube part 12 is constant.

In the embodiment described above, the base end of the half tube part 7a and the flange part 7b are fixed to the lower jaw side attachment body 3 and the base end of the half tube part 8a and the flange part 8b are fixed to the upper jaw side attachment body 2 by potting using resin for a dental technique. However, the present invention is not limited to this embodiment. For example, the base end of the half tube part 7a and the flange part 7b may be fixed to the lower jaw side attachment body 3 and the base end of the half tube part 8a and the flange part 8b may be fixed to the upper jaw side attachment body 2 by an adhesive having no biological toxicity (or low biological toxicity) other than the resin for a dental technique. Also in this case, an area of a portion of the base member 7 fixed to the lower jaw side attachment body 3 can be made wider by utilizing the flange part 7b and, in addition, an area of a portion of the slide member 8 fixed to the upper jaw side attachment body 2 can be made wider by utilizing the flange part 8b. Therefore, similarly to the embodiment described above, the fixed strength of the adjuster 4 to the upper jaw side attachment body 2 and the lower jaw side attachment body 3 can be secured.

In the embodiment described above, the base member 7 is fixed to the lower jaw side attachment body 3 and the slide member 8 is fixed to the upper jaw side attachment body 2. However, it may be structured that the base member 7 is fixed to the upper jaw side attachment body 2 and the slide member 8 is fixed to the lower jaw side attachment body 3. Further, in the embodiment described above, the flange part 7b is integrally formed with the half tube part 7a, and the flange part 8b is integrally formed with the half tube part 8a. However, the flange part 7b which is separately formed from the half tube part 7a may be fixed to the half tube part 7a and the flange part 8b which is separately formed from the half tube part 8a may be fixed to the half tube part 8a. Further, in the embodiment described above, all parts of the adjuster 4 are formed of synthetic resin. However, a part formed of metal having no biological toxicity (or low biological toxicity) such as titanium or stainless steel may be included in parts of the adjuster 4.

What is claimed is:

1. An adjuster for an airway securing device which is used in the airway securing device having an upper jaw side attachment body configured to be worn on an upper jaw side in an oral cavity of a patient and a lower jaw side attachment body configured to be worn on a lower jaw side in the oral cavity of the patient, the adjuster comprising:
    a base member configured to be fixed to a first one of the upper jaw side attachment body and the lower jaw side attachment body;
    a slide member configured to be fixed to a second one of the upper jaw side attachment body and the lower jaw side attachment body and capable of sliding with respect to the base member; and
    an adjusting bolt configured to slide the slide member with respect to the base member;
    wherein the base member is provided with a base member side half tube part which is formed in a substantially half tube shape;
    wherein the slide member is provided with a slide member side half tube part which is formed in a substantially half tube shape;
    wherein the base member side half tube part and the slide member side half tube part form a tube part in a substantially tube shape in which the adjusting bolt is disposed on an inner peripheral side;
    wherein a base end of the base member side half tube part configured to be fixed to the first one of the upper jaw side attachment body and the lower jaw side attachment body is formed with a base member side flange part which is enlarged in a flange shape;
    wherein a base end of the slide member side half tube part configured to be fixed to the second one of the upper jaw side attachment body and the lower jaw side attachment body is formed with a slide member side flange part which is enlarged in a flange shape;
    wherein an abutting face of the base member side flange part is configured to be abutted with the first one of the upper jaw side attachment body and the lower jaw side attachment body, and
    an abutting face of the slide member side flange part is configured to be abutted with the second one of the upper jaw side attachment body and lower jaw side attachment body.

2. The adjuster for an airway securing device according to claim 1, wherein
    the base member side flange part and the slide member side flange part are provided with curved plate parts which are enlarged along tooth rows of the patient.

3. The adjuster for an airway securing device according to claim 2, wherein
    the base member side flange part is formed with a through-hole penetrating through the base member side flange part, and
    the slide member side flange part is formed with a through-hole penetrating through the slide member side flange part.

4. The adjuster for an airway securing device according to claim 2, wherein
    an outward form of the tube part becomes smaller as going toward a tip end of the tube part from a base end of the tube part, wherein
    the tip end of the tube part is configured to be fixed to the upper jaw side attachment body and the lower jaw side attachment body.

5. The adjuster for an airway securing device according to claim 2, wherein
    the adjusting bolt is rotatably held by the base member, and
    a tip end of the adjusting bolt disposed on a tip end side of the base member side half tube part is disposed on a base end side of the base member side half tube part relative to a tip end of the base member side half tube part.

6. The adjuster for an airway securing device according to claim 2, wherein all parts including the adjusting bolt are formed of synthetic resin.

7. An airway securing device comprising:
    the adjuster for an airway securing device as defined in claim 2;
    the upper jaw side attachment body; and
    the lower jaw side attachment body;
    wherein the base member side flange part is fixed to the first one of the upper jaw side attachment body and the lower jaw side attachment body by potting resin which covers the base member side flange part; and
    wherein the slide member side flange part is fixed to the second one of the upper jaw side attachment body and the lower jaw side attachment body by potting resin which covers the slide member side flange part.

8. The adjuster for an airway securing device according to claim 1, wherein
    the base member side flange part is formed with a through-hole penetrating through the base member side flange part, and
    the slide member side flange part is formed with a through-hole penetrating through the slide member side flange part.

9. The adjuster for an airway securing device according to claim 1, wherein
    an outward form of the tube part becomes smaller as going toward a tip end of the tube part from a base end of the tube part, wherein
    the tip end of the tube part is configured to be fixed to the upper jaw side attachment body and the lower jaw side attachment body.

10. The adjuster for an airway securing device according to claim 1, wherein
    the adjusting bolt is rotatably held by the base member, and
    a tip end of the adjusting bolt disposed on a tip end side of the base member side half tube part is disposed on a base end side of the base member side half tube part relative to a tip end of the base member side half tube part.

11. The adjuster for an airway securing device according to claim 1, wherein all parts including the adjusting bolt are formed of synthetic resin.

12. An airway securing device comprising:
the adjuster for an airway securing device as defined in claim 1;
the upper jaw side attachment body; and
the lower jaw side attachment body;
wherein the base member side flange part is fixed to the first one of the upper jaw side attachment body and the lower jaw side attachment body by potting resin which covers the base member side flange part; and
wherein the slide member side flange part is fixed to the second one of the upper jaw side attachment body and the lower jaw side attachment body by potting resin which covers the slide member side flange part.

* * * * *